US012767922B2

(12) United States Patent
Choi et al.

(10) Patent No.: US 12,767,922 B2
(45) Date of Patent: *Oct. 20, 2026

(54) ***SCHIZOCHYTRIUM* SP. STRAIN AND POLYUNSATURATED FATTY ACID PRODUCTION METHOD USING SAME**

(71) Applicant: CJ CHEILJEDANG CORPORATION, Seoul (KR)

(72) Inventors: Jung Woon Choi, Seoul (KR); Sung Hoon Jang, Seoul (KR); Ji Young Kim, Seoul (KR); Won Sub Shin, Seoul (KR); Hae Won Kang, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 492 days.

This patent is subject to a terminal disclaimer.

(21) Appl. No.: 18/255,943

(22) PCT Filed: Nov. 8, 2021

(86) PCT No.: PCT/KR2021/016156

§ 371 (c)(1),
(2) Date: Jun. 5, 2023

(87) PCT Pub. No.: WO2022/124590

PCT Pub. Date: Jun. 16, 2022

(65) Prior Publication Data

US 2024/0101953 A1 Mar. 28, 2024

(30) Foreign Application Priority Data

Dec. 7, 2020 (KR) ........................ 10-2020-0169850

(51) Int. Cl.

| | |
|---|---|
| ***C12N 1/125*** | (2026.01) |
| ***A23K 10/16*** | (2016.01) |
| ***C12P 7/6409*** | (2022.01) |
| ***C12P 7/6432*** | (2022.01) |
| ***C12P 7/6434*** | (2022.01) |
| ***C12R 1/89*** | (2006.01) |

(52) U.S. Cl.

CPC .............. *C12N 1/125* (2021.05); *A23K 10/16* (2016.05); *C12P 7/6409* (2013.01); *C12P 7/6432* (2022.01); *C12P 7/6434* (2022.01); *C12R 2001/89* (2021.05)

(58) Field of Classification Search

None

See application file for complete search history.

(56) References Cited

U.S. PATENT DOCUMENTS

| | | | |
|---|---|---|---|
| 10,023,884 B2 | 7/2018 | Ujihara et al. | |
| 2008/0032361 A1 | 2/2008 | Bailey et al. | |
| 2015/0104557 A1 | 4/2015 | Rusing et al. | |
| 2016/0208297 A1 | 7/2016 | Ogawa et al. | |
| 2018/0016605 A1* | 1/2018 | Comini | A23K 20/158 |
| 2018/0289652 A1 | 10/2018 | Apt et al. | |
| 2021/0002680 A1 | 1/2021 | Kim et al. | |
| 2023/0242836 A1 | 8/2023 | Diehl et al. | |
| 2023/0392108 A1 | 12/2023 | Shin et al. | |

FOREIGN PATENT DOCUMENTS

| | | | |
|---|---|---|---|
| CL | 2020002416 | A1 | 12/2020 |
| CL | 2022003599 | A1 | 8/2023 |
| CL | 2023001619 | A1 | 1/2024 |
| CN | 104995291 | A | 10/2015 |
| CN | 111235035 | A | 6/2020 |
| EA | 011858 | B1 | 6/2009 |
| EA | 035287 | B1 | 5/2020 |
| KR | 1020170032577 | A | 3/2017 |
| KR | 101847551 | B1 | 4/2018 |
| KR | 1020190110186 | A | 9/2019 |
| RU | 2326171 | C2 | 6/2008 |

OTHER PUBLICATIONS

Tarantul V.Z. Explanatory biotechnological dictionary. Russian-English.—M.: Languages of Slavic cultures, 2009. -936, pp. 331, 380, ISBN 978-5-9551-0342-6.

Kuznetsova E.A, Brackets in Text of Legal Document as a Linguistic and Cognitive Phenomenon, Jan. 20, 2015.

Russian Office Action for Russian Patent Application No. 2023111156 dated Jan. 23, 2024.

Office Action issued on Oct. 2, 2024 in Chile, by INAPI (Instituto Nacional de Propiedad Industrial) for Application No. 202301623.

Korean Office Action in KR 10-2020-0169850 dated Apr. 17, 2023.

Korean Office Action in KR 10-2020-0169850 dated Dec. 20, 2022.

Korean Office Action in KR 10-2020-0169850 dated Jun. 22, 2022.

Park et al., "Enhanced production of carotenoids using a Thraustochytrid microalgal strain containing high levels of docosahexaenoic acid-rich oil", Bioprocess and Biosystems Engineering , 2018, 41, pp. 1355-1370.

Park, "Isolation and Mutagenesis of *Schizochytrium* sp. for High Production of Carotenoid Pigments", Department of Biotechnology, The Graduate School, Chonbuk National Univ., Feb. 22, 2017, 12 pages.

Japanese Office Action for Japanese Patent Application No. 2023-533260 dated Jun. 4, 2024 with English Translation.

Kazuo Watanabe et al., "Production of 13C-Labeled Docosahexaenoic Acid by a Thraustochytrid", J. Jpn. Oil Chem. Soc., vol. 49, No. 11/12, 2000, 1437-1449.

(Continued)

*Primary Examiner* — Robert J Yamasaki
*Assistant Examiner* — Charles Zoltan Constantine
(74) *Attorney, Agent, or Firm* — Morgan, Lewis & Bockius LLP

(57) ABSTRACT

The present application relates to a novel strain of the genus *Schizochytrium* (*Schizochytrium* sp.) and a method of producing polyunsaturated fatty acids by using the same. According to one aspect, novel microalgae of the genus *Schizochytrium* have a high content of fat in biomass, and particularly, a high content of polyunsaturated fatty acids such as docosahexaenoic acid (DHA) and eicosapentaenoic acid (EPA), and therefore, the microalgae, and biomass or bio-oil prepared therefrom, may be useful as a feed source or the like.

14 Claims, 3 Drawing Sheets

Specification includes a Sequence Listing.

(56) References Cited

OTHER PUBLICATIONS

European Search Report for European Patent Application No. 21903637.3 dated Jul. 18, 2025.
Adam M. Burja et al., “Isolation and characterization of polyunsaturated fatty acid producing *fhramtochytrmm* species» screening of strains and optimization of omega»3 production”,Appl Microbiol Biotechnol (2006) 72: 1161-1169.
Kim Jye Lee Chang et al., “Biodiscovery of new Australian thraustochytrids for production of biodiesel and long-chain omega-3 oils”,Appi Microbiol Biotechnol (2012) 93:2215-2231.
Office Action issued in corresponding Chinese Patent Application No. 202180079542.0, dated Jun. 2, 2026.
Chang et al., “Optimization of cultivation conditions for efficient production of carotenoid-rich DHA oil by Schizochytrium sp. S31”, Process Biochemistry, vol. 94, Apr. 25, 2020, pp. 190-197.
Yuan et al., “Rapid Mutation Breeding Schizochytrium Strains Producing High-yield Docosahexenoic Acid by Atmospheric and Room Temperature Plasmas (ARTP)”, Biotechnology Bulletin, vol. 31, No. 10, Oct. 28, 2015, pp. 199-204 with an English Abstract.

* cited by examiner

SEQUENCE LISTING

<160> NUMBER OF SEQ ID NOS: 3

<210> SEQ ID NO 1
<211> LENGTH: 1784
<212> TYPE: RNA
<213> ORGANISM: Schizochytrium aggregatum

<400> SEQUENCE: 1
aucugguuga uccugccagu agucauaugc ucgucucaaa gauuaagcca ugcaugugua 60
aguauaagcg auuguacugu gagacugcga acggcucauu auaucaguaa uaauuucuuc 120
gguaguuucu uuuauaugga uaccugcagu aauucuggaa auaauacaug cuguaagagc 180
ccuguauggg gcugcacuua uuagauugaa gccgauuuua uuggugaauc augauaauug 240
agcagauuga cuauuugguc gaugaaucgu uugaguuucu gccccaucag uugucgacgg 300
uaguguauug gacuacggug acuauaacgg gugacggaga guuagggcuc gacuccggag 360
agggagccug agagacggcu accauaucca aggauagcag caggcgcgua aauuacccac 420
uguggacucc acgagguagu gacgagaaau aucgaugcga agcguguaug cguuuugcua 480
ucggaaugag agcaauguaa aacccucauc gaggaucaac uggagggcaa gucuggugcc 540
agcagccgcg guaauuccag cuccagaagc auaugcuaaa guuguugcag uuaaaaagcu 600
cguaguugaa uuucuggcau gggcgaccgg ugcuuucccu gaauggggau ugauugucug 660
uguugccuug gccaucuuuu ucuuuucuuu auaggggaga aaucuuucac uguaaucaaa 720
gcagaguguu ccaagcaggu cguaugaccg guauguuuau uaugggauga uaagauagga 780
cuugggugcu auuuuguugg uuugcacgcc ugaguaaugg uuaauaggaa caguuggggg 840
uauucguauu uaggagcuag aggugaaauu cuuggauuuc cgaaagacga acuagagcga 900
aggcauuuac caagcauguu uucauuaauc aagaacgaaa gucuggggau cgaagaugau 960
uagauaccau cguagucuag accguaaacg augccgacuu gcgauuguug ggugcuuuuu 1020
uaugggccuc agcagcagca caugagaaau caaagucuuu ggguuccggg gggaguaugg 1080
ucgcaaggcu gaaacuuaaa ggaauugacg gaagggcacc accaggagug gagccugcgg 1140
cuuaauuuga cucaacacgg gaaaacuuac cagguccaga cauagguagg auugacagau 1200
ugagagcucu uucaugauuc uaugggugggu ggugcauggc cguucuuagu ugguggagug 1260
auuugucugg uuaauuccgu uaacgaacga gaccucggcc uacuaaauag ugcgugguau 1320
ggcaacauag uacguuuuaa cuucuuagag ggacaugucc gguuuacggg caggaaguuc 1380
gaggcaauaa caggucugug augcccuuag auguucuggg ccgcacgcgc gcuacacuga 1440
uggguucauc ggguuuuaau ucuguuuuua uggaauugag ugcuuggucg gaaggccugg 1500
cuaauccuug gaacgcucau cgugcugggg cuagauuuuu gcaauuauua aucuccaacg 1560
aggaauuccu aguaaacgca agucaucagc uugcauugaa uacgucccug cccuuuguac 1620

-continued

```
acaccgcccg ucgcaccuac cgauugaacg guccgaugaa accaugggau guuucuguuu   1680

ggauuaauuu uuggacagag gcagaacucg ggugaaucuu auuguuuaga ggaaggugaa   1740

gucguaacaa gguuuccgua ggugaaccug cggaaggauc auua                    1784


<210> SEQ ID NO 2
<211> LENGTH: 22
<212> TYPE: DNA
<213> ORGANISM: Artificial Sequence
<220> FEATURE:
<223> OTHER INFORMATION: PCR primer 18s-001F

<400> SEQUENCE: 2

aacctggttg atcctgccag ta                                              22


<210> SEQ ID NO 3
<211> LENGTH: 25
<212> TYPE: DNA
<213> ORGANISM: Artificial Sequence
<220> FEATURE:
<223> OTHER INFORMATION: PCR primer 18s-013R

<400> SEQUENCE: 3

ccttgttacg acttcacctt cctct                                           25
```

*SCHIZOCHYTRIUM* SP. STRAIN AND POLYUNSATURATED FATTY ACID PRODUCTION METHOD USING SAME

CROSS-REFERENCE TO RELATED APPLICATIONS

The present application is a U.S. national phase application of International Application No. PCT/KR2021/016156 filed on Nov. 8, 2021, which claims priority to/from and the benefit of Korean Application No. 10-2020-0169850 filed on Dec. 7, 2020, each of which is incorporated herein by reference in its entirety for all purposes.

SEQUENCE LISTING

The present application contains a Sequence Listing which has been submitted electronically in ASCII format and is hereby incorporated by reference in its entirety. Said ASCII copy, created on Jun. 1, 2023, is named "96N1879.TXT" and is 3,274 bytes in size.

TECHNICAL FIELD

The present application relates to novel strains of the genus *Schizochytrium* (*Schizochytrium* sp.) and a method of producing polyunsaturated fatty acids by using the same.

BACKGROUND ART

Unsaturated fatty acids are fatty acids having one or more double bonds in the fatty acid chain, and unsaturated fatty acids including two or more double bonds are called polyunsaturated fatty acids (PUFA). Among polyunsaturated fatty acids, docosahexaenoic acid (DHA) and eicosapentaenoic acid (EPA) are typical omega-3 fatty acids, which are essential for the brain, ocular tissue, and nervous system. In addition, they are known to play an important role in the development of the nervous system, such as visual acuity and motor neuron ability in infants, and prevention of cardiovascular diseases, and are the most abundant component in the structural lipids of the brain.

Most higher organisms, including humans, cannot synthesize polyunsaturated fatty acids on their own, so polyunsaturated fatty acids must be consumed as essential nutrients, and are mainly supplied from deep-sea fish, which occupy the upper ranks of the marine ecological environment, such as tuna and salmon. The main industrial source of polyunsaturated fatty acids identified so far is fish oil extracted from oils of blue fish such as mackerel, saury, tuna, horse mackerel, sardines, and herring, which is also very useful for fish feed such as saltwater fish initial feed. However, the quality of fish oil varies depending on the species, season, and fishing location, and there is difficulty in supplying fish oil continuously, and due to issues of contamination of fish oil by heavy metals and organic chemicals, the unique fishy smell of fish oil, and limited production due to oxidation of double bonds during processing processes, the need for alternative resources of polyunsaturated fatty acids is emerging.

In order to solve these issues, research on methods of producing polyunsaturated fatty acids including docosahexaenoic acid by microbial culture is currently being conducted. In particular, microalgae can produce lipids and are easily cultured, enabling production of biomass having a relatively constant biochemical composition. In addition, lipids produced by microalgae do not have an unpleasant odor like fish oil, and have a simpler fatty acid composition than fish oil, so it may be easy to separate specific fatty acids. Accordingly, new microalgae capable of stably supplying a specific fatty acid at a high level are of great value industrially, and thus, it is necessary to develop such microalgae.

DISCLOSURE

Technical Problem

An object of the application is to provide microalgae of the genus *Schizochytrium* (*Schizochytrium* sp.) which are deposited under an accession number of KCTC14344BP or KCTC14345BP; and are capable of producing docosahexaenoic acid (DHA), eicosapentaenoic acid (EPA), and palmitic acid (PA).

Another object of the present application is to provide biomass derived from the microalgae of the genus *Schizochytrium* and a feed composition including the same.

Still another object of the present application is to provide a method of preparing biomass or bio-oil derived from the microalgae of the genus *Schizochytrium.*

Technical Solution

Each description and embodiment disclosed in the application may also be applied to other descriptions and embodiments. That is, all combinations of various elements disclosed in the application fall within a scope of the application. In addition, it should not be construed that the scope of the present application is limited by the detailed description described below. In addition, those skilled in the art will recognize, or confirm many equivalents to specific aspects of the present application described herein, by using only experiments known in the art. Also, such equivalents are intended to be included in this application.

An aspect provides microalgae of the genus *Schizochytrium* having an ability to produce docosahexaenoic acid, eicosapentaenoic acid, and palmitic acid; and is deposited under an accession number of KCTC14344BP or KCTC14345BP.

The term "Thraustochytrid", used herein, refers to microalgae of an order Thraustochytriales. In addition, the term "genus *Schizochytrium* (*Schizochytrium* sp.)", used herein, is one of genus names belonging to a Thraustochytriaceae family of the Thraustochytriales order, and may be used interchangeably with a term "genus *Schizochytrium*". In addition, the term "microalgae" refers to organisms that photosynthesize with chlorophyll, that live freely floating in water, which cannot be seen with the naked eye but can only be seen through a microscope, and the microalgae is also called phytoplanktons.

The term "docosahexaenoic acid (DHA)", used herein, refers to one of polyunsaturated fatty acids having a formula of $C_{22}H_{32}O_2$, and is one of omega-3 fatty acids along with alpha-linolenic acid (ALA) and eicosapentaenoic acid (EPA), its common name is cervonic acid, and may also be written as 22:6 n-3 as an abbreviation.

The term "eicosapentaenoic acid (EPA)", used herein, refers to one of polyunsaturated fatty acids having a formula of $C_{20}H_{30}O_2$, and is one of omega-3 fatty acids along with ALA and DHA, and may also be written as 20:5 n-3 as an abbreviation.

The term "palmitic acid (PA)", used herein, refers to one of saturated fatty acids having a formula of $C_{16}H_{32}O_2$.

The microalgae of the genus *Schizochytrium* may be a novel wild-type microalgae CD01-5000 of the genus

*Schizochytrium* deposited under an accession number of KCTC14344BP or a variant thereof, microalgae CD01-5004 of the genus *Schizochytrium* deposited under an accession number of KCTC14345BP.

The microalgae of the genus *Schizochytrium* may have a 18S rRNA nucleotide sequence of SEQ ID NO: 1, but is not limited thereto. For example, the microalgae of the genus *Schizochytrium* may have 18S rRNA consisting of a nucleotide sequence showing sequence identity with the nucleotide sequence of SEQ ID NO: 1 of 80% or more, 85% or more, 90% or more, 95% or more, 98% or more, or 99% or more, but is not limited thereto.

The microalgae of the genus *Schizochytrium* may produce 35 wt % to 60 wt % of DHA, based on a total weight of fatty acids. For example, the microalgae of the genus *Schizochytrium* may produce 40 wt % to 60 wt %, 45 wt % to 60 wt %, 50 wt % to 60 wt %, 35 wt % to 58 wt %, 40 wt % to 58 wt %, 45 wt % to 58 wt %, or 50 wt % to 58 wt % of DNA, based on a total weight of fatty acids. In addition, the microalgae of the genus *Schizochytrium* may include 35 wt % to 60 wt % of DHA, based on a total weight of fatty acids.

The microalgae of the genus *Schizochytrium* may produce 0.5 wt % to 10 wt % of EPA, based on a total weight of fatty acids. For example, the microalgae of the genus *Schizochytrium* may produce 0.5 wt % to 8 wt %, 0.5 wt % to 5 wt %, 0.5 wt % to 3 wt %, 0.8 wt % to 10 wt %, 0.8 wt % to 8 wt %, 0.8 wt % to 5 wt %, 0.8 wt % to 3 wt %, 1 wt % to 10 wt %, 1 wt % to 8 wt %, 1 wt % to 5 wt %, or 1 wt % to 3 wt % of EPA, based on a total weight of fatty acids. In addition, the microalgae of the genus *Schizochytrium* may include 0.5 wt % to 10 wt % of EPA, based on a total weight of fatty acids.

The microalgae of the genus *Schizochytrium* may produce 10 wt % to 30 wt % of PA, based on a total weight of fatty acids. For example, the microalgae of the genus *Schizochytrium* may produce 15 wt % to 30 wt %, or 20 wt % to 30 wt % of PA, based on a total weight of fatty acids. In addition, the microalgae of the genus *Schizochytrium* may include 10 wt % to 30 wt % of PA, based on a total weight of fatty acids.

The microalgae of the genus *Schizochytrium* may have a carotenoid-producing ability. For example, the microalgae of the genus *Schizochytrium* may produce at least one selected from the group consisting of β-carotene, lutein, astaxanthin, capsanthin, annatto, canthaxanthin, lycopene, β-apo-8-carotenal, zeaxanthin, and β-apo-8-carotenal-ester.

The term "carotenoid", used herein, refers to a pigment of the terpenoids synthesized from phytoene composed of 40 carbon atoms, and is produced from microorganisms such as microalgae and bacteria, or fungi such as mold and mushrooms, and higher organisms. Carotenoids are widely used as feed or food additives because of their unique color, and have a strong antioxidant effect due to their long double bond chain and ketone group (C═O) or hydroxyl group (—OH), and thus, are also studied as medicines and health foods. Carotenoids include β-carotene, lutein, astaxanthin, capsanthin, annatto, canthaxanthin, lycopene, β-apo-8-carotenal, zeaxanthin, or β-apo-8-carotenal-ester, etc.

Other aspects provide: microalgae of the genus *Schizochytrium* deposited under an accession number of KCTC14344BP or KCTC14345BP, and having an ability to produce docosahexaenoic acid, eicosapentaenoic acid, and palmitic acid; and biomass derived from the microalgae of the genus *Schizochytrium* including cultures of the microalgae, dried products of the cultures, or lysates of the dried products.

The microalgae of the genus *Schizochytrium* are as described above.

The term "biomass", used herein, refers to organisms such as plants, animals, and microorganisms that may be used as chemical energy, that is, an energy source of bioenergy, and ecologically refers to weight or amount of energy of a specific organism that exists within a unit time and space. In addition, the biomass includes, but is not limited to, compounds secreted by cells, and may contain cells and/or intracellular contents as well as extracellular materials. In the present application, the biomass may be microalgae of the genus *Schizochytrium* themselves, a culture thereof, a dried product thereof, a lysate thereof, or a product produced by culturing or fermenting the microalgae, or may be a concentrate or dried product of the biomass, but is not limited thereto.

The term "culture" of the microalgae of the genus *Schizochytrium* refers to a product produced by culturing the microalgae, specifically, the term may refer to a culture medium including the microalgae or a culture filtrate in which the microalgae are removed from the culture medium, but is not limited thereto. The "dried product" of the culture of the microalgae of the genus *Schizochytrium* may be one in which moisture has been removed from the culture of the microalgae for example, in a form of a dried cells of the microalgae, but is not limited thereto. In addition, "lysate" of the dried product is a generic term for resulting products of crushing the dried material in which moisture is removed from the culture of the microalgae, and may be, for example, powder of dried ells, but is not limited thereto. The culture of the microalgae of the genus *Schizochytrium* may be prepared by inoculating the microalgae in a microalgae culture medium and culturing according to culturing methods known in the art, and dried products of the culture and lysates thereof may be prepared by treating, or drying methods of the microalgae or culture medium known in the art.

Biomass derived from the microalgae of the genus *Schizochytrium* may include 35 wt % to 60 wt % of DHA, based on a total weight of fatty acids, may include 0.5 wt % to 10 wt % of EPA, based on a total weight of fatty acids, and may include 10 wt % to 30 wt % of PA, based on a total weight of fatty acids.

In addition, the biomass derived from the microalgae of the genus *Schizochytrium* may include carotenoids, for example, at least one selected from the group consisting of 6-carotene, lutein, astaxanthin, capsanthin, annatto, canthaxanthin, lycopene, β-apo-8-carotenal, zeaxanthin, and β-apo-8-carotenal-ester.

The biomass may be produced by a method of producing biomass derived from microalgae of the genus *Schizochytrium* according to an aspect.

Another aspect provides a composition including the microalgae of the genus *Schizochytrium*, cultures of the microalgae, dried products of the cultures, or lysates of the dried products, the microalgae being deposited under an accession number of KCTC14344BP or KCTC14345BP, and having an ability to produce docosahexaenoic acid, eicosapentaenoic acid, and palmitic acid. The composition may include biomass or bio-oil derived from the microalgae of the genus *Schizochytrium.*

Another aspect provides a feed composition including biomass derived from the microalgae of the genus *Schizochytrium*, or concentrates or dried products of the biomass, the microalgae being deposited under an accession number of KCTC14344BP or KCTC14345BP, and having an ability to produce docosahexaenoic acid, eicosapentaenoic acid, and palmitic acid.

The microalgae of the genus *Schizochytrium*, the biomass, the culture of the microalgae, the dried product of the culture, and the lysate of the dried product are as described above.

The concentrate or dried product of the biomass may be prepared according to methods of treating, concentrating, or drying microbial biomass known in the art.

The term "bio-oil", used herein, refers to oil obtained from biomass by biological, thermochemical, and physicochemical extraction processes, and bio-oil prepared in this application may contain polyunsaturated fatty acids, specifically, may contain DHA and EPA, but is not limited thereto.

The composition may be in a form of a solution, powder, or suspension, but is not limited thereto. The composition may be, for example, a food composition, a feed composition, or a feed additive composition.

The term "feed composition", used herein, refers to a feed fed to animals. The feed composition refers to a material that supplies organic or inorganic nutrients necessary for maintaining life of animals, or producing meat, milk, and the like. The feed composition may additionally include necessary nutrients for maintaining life of animals or producing meat, milk, and the like. The feed composition may be prepared as feeds of various forms known in the art, and specifically, the forms may include concentrated feeds, coarse fodders, and/or special feeds.

The term "feed additive", used herein, includes a substance added to a feed for various purposes, such as supplementation of nutrients, prevention of weight loss, enhancement of digestibility of fiber in the feed, improvement of oil quality, prevention of reproductive disorders, improvement of conception rates, and prevention of high temperature stress in summer, etc. The feed additive of the present application corresponds to a supplementary feed under the Feed Management Act, and may additionally include mineral preparations such as sodium bicarbonate, bentonite, magnesium oxide, complex minerals, etc., trace mineral preparations such as zinc, copper, cobalt, selenium, etc., vitamin preparations such as carotene, vitamin E, vitamins A, D, E, nicotinic acid, vitamin B complex, etc., protected amino acid preparations such as methionine and lysine, etc., protected fatty acids such as fatty acid calcium salts, etc., live bacteria such as probiotics (lactic acid bacteria), yeast cultures mold fermented products, etc., yeasts, etc.

The term "food composition", used herein, includes all forms of functional foods, nutritional supplements, health foods, and food additives, etc., and the above types of food composition may be prepared in various forms according to a common method known in the art.

The compositions of the present application may further include grains such as milled or crushed wheat, oats, barley, corn, and rice; vegetable protein feeds such as feeds having soybeans and sunflower as main ingredients; animal protein feed such as blood meal, meat meal, bone meal and fish meal; sugar and dairy products, for example, dry ingredients composed of various powdered milk and whey powder, etc., and may further include nutritional supplements, digestion and absorption enhancers, growth promoters, etc.

The composition of the present application may be administered to animals alone or in combination with other feed additives in an edible carrier. In addition, the composition may be easily administered to animals as a top dressing or by being directly mixed in a feed, or as an oral formulation separate from a feed. When the composition is administered separately from a feed, the composition may be prepared as an immediate release or sustained release formulation by combining with a pharmaceutically acceptable edible carrier as well known in the art. Such an edible carrier may be solid or liquid, and may be for example, corn starch, lactose, sucrose, soybean flakes, peanut oil, olive oil, sesame oil, and propylene glycol. When a solid carrier is used, the composition may be a tablet, capsule, powder, troche, or sugar-containing tablet, or a top dressing in a microdispersible form. When a liquid carrier is used, the composition may be in a form of a gelatin soft capsule, or a syrup, suspension, emulsion, or solution.

The composition of the present application may contain, for example, a preservative, a stabilizer, a wetting or emulsifying agent, a cryoprotectant, or an excipient, etc. The cryoprotectant may be at least one selected from the group consisting of glycerol, trehalose, maltodextrin, skim milk powder, and starch.

The preservative, stabilizer, or excipient may be included in the composition in an effective amount sufficient to reduce deterioration of the microalgae of the genus *Schizochytrium* included in the composition. In addition, the cryoprotectant may be included in the composition in an effective amount sufficient to reduce deterioration of the microalgae of the genus *Schizochytrium* included in the composition when the composition is in a dried state.

The composition may be added to an animal feed by dripping, spraying, or mixing, and used.

The composition of the present application may be applied to diets of a number of animals including mammals, birds, fish, crustaceans, cephalopods, reptiles, and amphibians, but is not limited thereto. For example, the mammals may include pigs, cows, sheep, goats, laboratory rodents, pets, etc., the birds may include poultry, and the poultry may include chickens, turkeys, ducks, geese, pheasant, or quail, etc., but is not limited thereto. In addition, the fish may include commercially farmed fish and their fry, aquarium fish, and the like, and the crustaceans may include shrimps, barnacles, and the like, but are not limited thereto. In addition, the composition may be applied to a diet of rotifers, which are zooplankton.

Another aspect provides a method of preparing biomass derived from the microalgae of the genus *Schizochytrium*, including: culturing the microalgae; and recovering biomass from the microalgae, cultures of the microalgae, dried products of the culture, or lysates of the dried products, wherein the microalgae of the genus *Schizochytrium* are deposited under an accession number of KCTC14344BP or KCTC14345BP, and have an ability to produce docosahexaenoic acid, eicosapentaenoic acid, and palmitic acid.

The microalgae of the genus *Schizochytrium*, the biomass, the culture of the microalgae, the dried product of the culture, and the lysate of the dried product are as described above.

The term "culture", used herein, means to grow the microalgae under appropriately controlled environmental conditions. The culturing processes of the present application may be performed according to appropriate media and culture conditions known in the art. Theses culturing processes may be easily adjusted and used by those skilled in the art according to the selected microalgae.

Specifically, culturing of the microalgae of the genus *Schizochytrium* of the present application may be performed under heterotrophic conditions, but is not limited thereto.

The term "heterotrophic", used herein, refers to a mode of nutrition that relies on organic matters obtained from outside the body as an energy source or nutrient source, and is a term apposite to "autotrophic", and may be used interchangeably with the term 'dark culture'.

The culturing of the microalgae of the genus *Schizochytrium* may be performed by a known batch culture method, continuous culture method, fed-batch culture method, or the like, but is not particularly limited thereto. As a medium and other culture conditions used for culturing the microalgae of the present application, any medium used for culturing microalgae in the art may be used without particular limitation. Specifically, the microalgae of the present application may be cultured in a medium in the art containing appropriate carbon sources, nitrogen sources, phosphorus sources, inorganic compounds, amino acids, and/or vitamins, etc., while controlling temperature, pH, etc., under aerobic conditions.

Specifically, an appropriate pH (for example, pH 5 to 9, specifically pH 6 to 8, most specifically pH 6.8) may be adjusted by using a basic compound (for example, sodium hydroxide, potassium hydroxide, or ammonia) or an acidic compound (for example, phosphoric acid, or sulfuric acid), but is not limited thereto.

In addition, in order to maintain the aerobic condition of the culture, oxygen or oxygen-containing gas may be injected into the culture, or in order to maintain an anaerobic and micro-aerobic state, gas may be not injected, or nitrogen, hydrogen, or carbon dioxide gas may be injected, but is not limited.

In addition, the culture may be maintained at a temperature of 20° C. to 45° C., or 25° C. to 40° C., and may be cultured for about 10 hours to 160 hours, but is not limited thereto. In addition, during the culturing, foaming may be suppressed by using an antifoaming agent such as fatty acid polyglycol ester, but is not limited thereto.

A carbon source included in the medium used in the culturing of the microalgae of the genus *Schizochytrium* may be at least one selected from the group consisting of glucose, fructose, maltose, galactose, mannose, sucrose, arabinose, xylose, and glycerol, but is not limited thereto, and any carbon source used for culturing microalgae may be used.

A nitrogen source included in the medium used in the culturing of the microalgae of the genus *Schizochytrium* may be: i) at least one organic nitrogen source selected from the group consisting of yeast extract, beef extract, peptone, and tryptone, or ii) at least one inorganic nitrogen source selected from the group consisting of ammonium acetate, ammonium nitrate, ammonium chloride, ammonium sulfate, sodium nitrate, urea, and monosodium glutamate (MSG), but is not limited thereto, and any nitrogen source used for culturing microalgae may be used.

In the medium used in the culturing of the microalgae of the genus *Schizochytrium*, as a phosphorus source, potassium dihydrogen phosphate, dipotassium hydrogen phosphate, sodium-containing salts corresponding thereto may be separately included or mixed, but is not limited thereto.

The recovering of biomass from the microalgae, a culture of the microalgae, a dried product of the culture, or a lysate of the dried product may be collecting desired biomass by using a suitable method known in the art. For example, centrifugation, filtration, anion exchange chromatography, crystallization, and high-performance liquid chromatography (HPLC), etc. may be used, and a purification process may be further included.

Another aspect provides a method of preparing bio-oil derived from the microalgae of the genus *Schizochytrium*, including: culturing the microalgae of the genus *Schizochytrium*; and recovering lipids from the microalgae, cultures of the microalgae, dried products of the culture, or lysates of the dried products, wherein the microalgae of the genus *Schizochytrium* are deposited under an accession number of KCTC14344BP or KCTC14345BP, and have an ability to produce docosahexaenoic acid, eicosapentaenoic acid, and palmitic acid.

The microalgae of the genus *Schizochytrium*, the bio-oil, the culture of the microalgae, the dried product of the culture, and the lysate of the dried product, and the culturing of the microalgae are as described above.

The recovering of lipids from the microalgae, a culture of the microalgae, a dried product of the culture, or a lysate of the dried product may be collecting desired lipids by using a suitable method known in the art. For example, centrifugation, filtration, anion exchange chromatography, crystallization, and HPLC, etc. may be used, and a purification process may be further included.

For example, lipids and lipid derivatives such as fatty aldehydes, fatty alcohols and hydrocarbons (for example, alkanes) may be extracted with a hydrophobic solvent such as hexane. The lipids and lipid derivatives may also be extracted by using methods such as liquefaction, oil liquefaction, and supercritical $CO_2$ extraction, etc. In addition, a known method of recovering microalgae lipids includes, for example, i) collecting cells by centrifugation, washing with distilled water, and drying by freeze drying, and ii) grinding the obtained cell powder, and then extracting lipids with n-hexane (Miao, X and Wu, Q, Biosource Technology (2006) 97:841-846).

Advantageous Effects

Novel microalgae of the genus *Schizochytrium* (*Schizochytrium* sp.) according to an aspect have a high content of fat in biomass, and particularly, a high content of polyunsaturated fatty acids such as docosahexaenoic acid (DHA) and eicosapentaenoic acid (EPA), and therefore, the microalgae, and biomass or bio-oil prepared therefrom may be useful as a feed source, etc.

MODE FOR INVENTION

Hereinafter, the present disclosure will be described in more detail through examples. However, these examples are intended to illustrate at least one specific example, and the scope of the present disclosure is not limited to these examples.

Example 1. Isolation of Microalgae which are Thraustochytrids

In order to isolate microalgae which are Thraustochytrids, environmental samples in a form of seawater, soil, and sediment were collected from a total of 50 coastal areas in Taean, Chungcheongnam-do, and Gunsan, Jeollabuk-do, Korea. The collected environmental samples were transported to a laboratory environment, and contaminants such as fungi, other bacterial microorganisms, and protozoa, etc.

were removed within 7 days, while direct plating and pine pollen baiting were used to isolate microalgae which are Thraustochytrids. During the process of continuous removal of contaminants and microalgae isolation, samples that show similar forms to cells that form zoospores and include the same, which are characteristics of microalgae which are Thraustochytrids, were isolated, and smeared on a modified yeast extract peptone (YEP) medium (1 g/L of yeast extract, 1 g/L of peptone, 2 g/L of $MgSO_4 \cdot 7H_2O$, 20 g/L of sea salt, 5.0 mg/L of $H_3BO_3$, 3.0 mg/L of $MnCl_2$, 0.2 mg/L of $CuSO_4$, 0.05 mg/L of $NaMo_4 \cdot 2H_2O$, 0.05 mg/L of $CoSO_4$, 0.7 mg/L of $ZnSO_4 \cdot 7H_2O$, and 15 g/L of agar), a medium for isolating marine microalgae. The obtained colonies were pure isolated by subculture several times. Colonies with persistent contamination were exposed to an antibiotic cocktail mix solution (0 mg/L to 100 mg/L of streptomycin sulfate, 0 mg/L to 100 mg/L of ampicillin, 0 mg/L to 100 mg/L of penicillin G, and 0 mg/L to 100 mg/L of kanamycin sulfate) to control and eliminate the contaminants. Through the above process, about 50 colonies were isolated and obtained.

Figure 1:
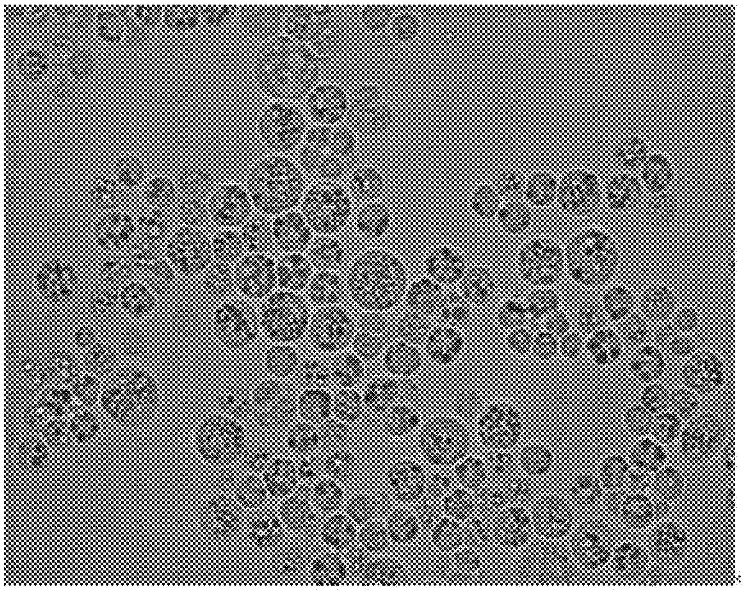
FIG. 1 is a photograph of a *Schizochytrium* sp. strain CD01-5000 observed under an optical microscope.

The pure isolated colonies were cultured in a 250 mL flask under conditions of 10° C. to 35° C. and 100 rpm to 200 rpm for about 7 days, by using a modified glucose yeast extract peptone (GYEP) medium (10 g/L of glucose, 1 g/L of yeast extract, 1 g/L of peptone, 2 g/L of $MgSO_4 \cdot 7H_2O$, 20 g/L of sea salt, 5.0 mg/L of $H_3BO_3$, 3.0 mg/L of $MnCl_2$, 0.2 mg/L of $CuSO_4$, 0.05 mg/L of $NaMo_4 \cdot 2H_2O$, 0.05 mg/L of $CoSO_4$, and 0.7 mg/L of $ZnSO_4 \cdot 7H_2O$). Among the colonies, one type of microalgae capable of growing at a temperature of 25° C. or higher, having an excellent growth rate, and from which a sufficient number of cells may be secured were finally selected and named CD01-5000. Morphology of the selected strain was observed by using an optical microscope (FIG. 1).

Example 2. Identification of a Novel *Schizochytrium* Sp. Strain CD01-5000

For molecular biological identification of the microalgal strain CD01-5000 isolated and selected in Example 1, the 18S rRNA gene sequence was analyzed.

Specifically, after extracting and separating gDNA from colonies of pure isolated microalgae CD01-5000, a PCR reaction was performed by using the primers shown in Table 1 below as primers for gene amplification of the 18S rRNA region.

TABLE 1

| Seq No. | Primer | Sequence (5' - 3') |
|---|---|---|
| 2 | 18s-001F | AACCTGGTTGATCCTGCCAGTA |
| 3 | 18s-013R | CCTTGTTACGACTTCACCTTCCTCT |

For the PCR reaction, denaturation at 95° C. for 5 minutes, followed by denaturation at 95° C. for 30 seconds, annealing at 55° C. for 30 seconds, and polymerization at 72° C. for 1 minute 30 seconds, were repeated 38 times, and then polymerization was performed at 72° C. for 5 minutes, by using a reaction solution containing taq polymerases. The reaction solution amplified through the PCR process was electrophoresed on 1% agarose gel to confirm that DNA fragments having a size of about 1600 bp to 2000 bp were amplified, and sequencing analysis was performed. As a result of the analysis, a nucleotide sequence of about 1800 bp in size (SEQ ID NO: 1) was obtained, and the corresponding sequence was confirmed to show homology of 99.3% with a 18S rRNA nucleotide sequence of a *Schizochytrium* limacinum strain OUC192 (NCBI accession No.: HM042913.2) belonging to microalgae which are Thraustochytrids, and homology of 99.3% with a 18S rRNA nucleotide sequence of a *Schizochytrium* sp. strain SH104 (NCBI accession No.: KX379459.1) through NCBI BLAST searches. Through this, it was confirmed that the isolated microalgae CD01-5000 is a novel strain of the genus *Schizochytrium*, and the strain was named *Schizochytrium* sp. CD01-5000, and on Oct. 26, 2020, was deposited with the Korean Collection for Type Cultures (KCTC), an international depository institution under the Budapest treaty, and was given an accession number of KCTC14344BP.

Example 3. Development of Mutant Microalgal Strains

Example 3-1. Measurement of Mortality Rate According to Irradiation of Gamma Rays In order to develop an artificial mutant strain from the novel microalgae CD01-5000 identified in Example 2, gamma irradiation conditions were selected by measuring mortality rates according to doses of gamma rays.

Specifically, the novel microalgae CD01-5000 were cultured in a modified GYEP medium containing 3% glucose for about 20 hours or more to reach an exponential phase. The cultured cell culture medium sample was centrifuged at 4,000 rpm for 15 minutes to harvest the cells, and the microalgae culture medium sample suspended in PBS to $10^9$ cells/mL was placed in a 50 mL conical tube and used for gamma irradiation experiments. The gamma ray irradiation experiments were conducted at the Advanced Radiation Research Center of the Korea Atomic Energy Research Institute, and gamma rays of 2000 Gy, 2500 Gy, 3000 Gy, 3500 Gy, 4000 Gy, 4500 Gy, 5000 Gy, 5500 Gy, 6000 Gy, 7000 Gy, or 8000 Gy were irradiated to the microalgae culture medium sample. After removing the supernatant by centrifuging the microalgae culture medium sample irradiated with gamma rays, the sample was inoculated into a GCBS medium containing 1% glucose (10 g/L of glucose, 5 g/L of corn steep liquor, 5 g/L of beef extract, 5 g/L of $MgSO_4 \cdot 7H_2O$, 15 g/L of sea salt, 20.08 mg/L of citric acid, 5.3 mg/L of $FeSO_4 \cdot 7H_2O$, 0.5 mg/L of $ZnSO_4 \cdot 7H_2O$, 1.0 mg/L of $MnCl_2$, 0.1 mg/L of $CuSO_4$, 0.1 mg/L of $NaMo_4 \cdot 2H_2O$, 0.1 mg/L of $CoSO_4$, 1.0 mg/L of biotin, 1.0 mg/L of thiamine hydrochloride, 1.0 mg/L of CAPA, and 0.1 mg/L of vitamin B12) and cultured at 30° C. for about 48 hours. Thereafter, the culture medium was inoculated and smeared on GYEP medium containing 2% (20 g/L) agar, and cultured at 30° C. for 48 hours, and then a number of growing colonies was counted and mortality rates according to doses of gamma rays were calculated by the following Equation 1.

$$\text{Mortality rate (\%)} = [\{(\text{Number of colonies in untreated group}) - (\text{Number of colonies in treated group})\}/(\text{Number of colonies in untreated group})] \times 100 \quad \text{Equation 1}$$

TABLE 2

| Gamma ray dose (Gy) | Number of growing colonies (EA) | Mortality rate (%) |
|---|---|---|
| 2000 | ≥90 | — |
| 2500 | ≥90 | — |
| 3000 | ≥90 | — |
| 3500 | ≥90 | — |
| 4000 | ≤10 | 90.5 |
| 4500 | ≤5 | 95.5 |
| 5000 | ≤3 | 98.89 |
| 5500 | ≤1 | 99.99 |
| 6000 | 0 | 100 |
| 7000 | 0 | 100 |
| 8000 | 0 | 100 |
| Untreated group (Ctrl) | ≥90 | 0 |

As a result, when gamma rays were irradiated at a dose of 6,000 Gy or more, microalgae were all killed and colonies could not be secured, and a gamma ray dose condition of 5,500 Gy was selected, which showed a mortality rate of 99.99%.

Example 3-2. Isolation of Mutant Microalgal Strains

After irradiating gamma rays at a dose of 5000 Gy to the novel microalgal strain CD01-5000 in the same manner as described in Example 3-1, the microalgal culture samples were inoculated and smeared on GYEP solid medium and GYEP solid medium supplemented with butanol and isoniazid, respectively, and cultured at 30° C. Microalgal colonies grown on each solid plate for about 4 weeks were selected and separated by subculturing in the same medium and culture conditions. Each colony separated by subculturing was judged as a different mutant strain, and colonies and strains capable of continuous growth were additionally selected.

Example 3-3. Selection of Excellent Mutant Microalgal Strains

Culture evaluation was performed on a flask scale for the mutant strains selected in Example 3-2, and an excellent mutant strain was selected through analyses of crude fat and fatty acids.

Specifically, in order to culture the novel wild-type microalgae CD01-5000 confirmed in Example 2 and the mutant microalgae selected in Example 3-2 on a flask scale, a working volume was set to 50 mL in a 500 mL flask, and in GYEP medium including 3% (30 g/L) glucose, the microalgae were cultured at 30° C. and 180 rpm for 24 hours to obtain a certain number of cells that may be analyzed. Thereafter, the culture medium was centrifuged by using a 50 mL conical tube, then the supernatant was removed, and the cells were collected and washed three times with PBS of pH 7.5, and then dried in a dry oven at 60° C. overnight to obtain each group of dried cells.

8.3 M of hydrochloric acid solution was added to 2 g of each group of the obtained dried cells to hydrolyze the cell walls of the microalgae cells at 80° C., and then processes of adding 30 mL of ethyl ether and 20 mL of petroleum ether, mixing for 30 seconds, and then centrifuging, were repeated three or more times. The separated solvent layer was collected, transferred to a pre-weighed round flask, and then the solvent was removed by nitrogen purging and dried in a desiccator until the weight became constant. A weight of the dried oil was measured by subtracting a weight of the empty flask from a weight of the flask after the drying. In addition, the obtained dried oil was pre-treated with 0.5 N of methanolic NaOH and 14% trifluoroboran methanol ($BF_3$), and then contents of the palmitic acid (PA), eicosapentaenoic acid (EPA), and docosahexaenoic acid (DHA) included in the oil were measured by using gas chromatography, and the content was calculated as a percentage relative to the total oil, that is, a weight of the crude fat.

TABLE 3

| | Fatty acid content based on crude fat (w/w %) | | |
|---|---|---|---|
| Strain | PA | EPA | DHA |
| Wildtype (CD01-5000) | 26.3 | 1.1 | 52.7 |
| Variant 1 | 23.4 | 0.5 | 17.6 |
| Variant 2 | 25.9 | 0.9 | 26.5 |
| Variant 3 (CD01-5004) | 26.2 | 1.4 | 56.3 |
| Variant 4 | 28.3 | 1.3 | 22.7 |
| Variant 5 | 28.1 | 1.5 | 25.2 |
| Variant 6 | 28.2 | 1.2 | 21.4 |
| Variant 7 | 29.0 | 1.5 | 22.9 |
| Variant 8 | 25.1 | 1.1 | 34.8 |
| Variant 9 | 11.8 | 0.6 | 11.5 |
| Variant 10 | 25.1 | 1.1 | 20.7 |
| Variant 11 | 24.4 | 0.7 | 33.0 |
| Variant 12 | 29.7 | 0.8 | 18.0 |
| Variant 13 | 29.6 | 1.2 | 21.4 |
| Variant 14 | 24.7 | 1.5 | 20.4 |
| Variant 15 | 28.7 | 0.6 | 16.9 |
| Variant 16 | 24.8 | 1.5 | 19.7 |
| Variant 17 | 24.8 | 1.5 | 21.4 |
| Variant 18 | 28.2 | 0.7 | 17.8 |
| Variant 19 | 29.9 | 0.6 | 17.9 |
| Variant 20 | 24.9 | 0.7 | 21.6 |
| Variant 21 | 22.4 | 1.6 | 19.5 |
| Variant 22 | 12.4 | 0.4 | 7.4 |

In Table 3, PA denotes palmitic acid, EPA denotes eicosapentaenoic acid, and DHA denotes docosahexaenoic acid.

As a result, as shown in Table 3, the novel *Schizochytrium* sp. strain CD01-5000 showed a very high DHA content of 50% or higher, and contents of palmitic acid and EPA were also shown to be higher than other variants. In addition, 'Variant 3' that showed DHA contents higher than the wild type strain, and also showed higher palmitic acid and EPA contents than other variants, was selected as an excellent variant among the experimented variants, named *Schizochytrium* sp. CD01-5004, and on Oct. 26, 2020, was deposited with the Korean Collection for Type Cultures (KCTC), an international depository institution under the Budapest treaty, and was given an accession number of KCTC14345B P.

Example 4. Confirmation of Culture Characteristics of Wild-Type *Schizochytrium* Sp. Strain CD01-5000, and Mutant *Schizochytrium* Sp. Strain CD01-5004

Additional culture characteristics of the novel wild-type *Schizochytrium* sp. strain CD01-5000, and a mutant thereof, *Schizochytrium* sp. strain CD01-5004, were confirmed.

Example 4-1. Analysis of Biomass and Fatty Acid Content

The CD01-5000 strain, the CD01-5004 strain, and a *Schizochytrium* sp. ATCC20888 strain, which is a control group, were cultured in a 5 L fermenter, until the total volume reached 3 L. The strains were cultured under conditions of 20° C. to 35° C., 100 rpm to 500 rpm, and 0.5 vvm to 1.5 vvm, in GYEP medium including 5 g/L of yeast extract and 10 g/L of peptone as nitrogen sources, and dried cells were obtained from the culture medium in the same manner as described in Example 3-3, and contents of intracellular crude fat and fatty acids were analyzed.

TABLE 4

| Strain | Weight of dried cells (g/L) | Fatty acids among crude fat (w/w %) EPA | DHA |
|---|---|---|---|
| *Schizochytrium* sp. ATCC20888 | 49.70 | 0.86 | 22.40 |
| *Schizochytrium* sp. CD01-5000 | 45.80 | 2.95 | 47.00 |
| *Schizochytrium* sp. CD01-5004 | 53.00 | 4.25 | 42.90 |

In Table 4, EPA denotes eicosapentaenoic acid, and DHA denotes docosahexaenoic acid.

As a result, as shown in Table 4, the CD01-5000 and CD01-5004 strains were confirmed to show biomass growth similar to the strain *Schizochytrium* sp. ATCC20888, which was cultured as a control group, while producing and accumulating high levels of EPA and DHA in the cells.

Example 4-2. Analysis of Contents of Proteins and Amino Acids

Additional culture tests were conducted on the CD01-5004 strain, which showed the highest biomass content and EPA content, in order to analyze contents of intracellular proteins and amino acids.

Specifically, the strain was cultured for a total of 63 hours under the same culturing conditions as described in Example 4-1, except that GYEP medium including 10 g/L of yeast extract and 10 g/L of ammonium chloride as nitrogen sources was used. After the culturing is ended, dried cells were obtained from the culture medium in the same manner as described in Example 3-3.

For an analysis of protein contents, nitrogen contents present in the sample were quantified by using an element analyzer for 0.5 g to 1.0 g of dried cells, respectively. A weight ratio (TN %) of nitrogen present in each sample was multiplied by 6.25 to calculate a content of crude proteins in the sample.

In order to analyze the amino acid content, 0.5 g to 1 g of each group of dried cells was acid hydrolyzed, and then liquid chromatography was performed thereto. A component ratio (%) of each amino acid was calculated as a percentage of each amino acid relative to the total amino acid concentration in the sample.

TABLE 5

| | |
|---|---|
| Weight of dried cells (g/L) | 60.5 |
| Crude protein (%) | 74.38 |
| Amino acid composition (%) | |
| Aspartic acid | 4.55 |
| Serine | 2.97 |
| Glutamate | 23.31 |
| Glycine | 3.65 |
| Alanine | 7.73 |
| Valine | 7.35 |
| Methionine | 5.03 |
| Isoleucine | 3.10 |

TABLE 5-continued

| | |
|---|---|
| Leucine | 3.53 |
| Phenylalanine | 20.51 |
| Histidine | 11.85 |
| Proline | 6.42 |

As a result, as shown in Table 5, total production of the cells was 60.5 g/L and the crude protein content in the dried cells was confirmed to be 74.38%. Intracellular amino acids were mainly composed of glutamate at 23.31% and phenylalanine at 20.51%, followed by histidine, alanine, valine, proline, methionine, aspartic acid, glycine, leucine, isoleucine, and serine.

Example 5. Confirmation of Growth Rate of Wild-Type *Schizochytrium* Sp. Strain CD01-5000, and Mutant *Schizochytrium* Sp. Strain CD01-5004

Growth rates of the novel wild-type *Schizochytrium* sp. strain CD01-5000, and a mutant thereof, *Schizochytrium* sp. strain CD01-5004, were measured and compared.

Specifically, CD01-5000 and CD01-5004 strains were each inoculated into GYEP medium containing 3% glucose so that the final working volume was 50 mL in a 500 mL flask, and cultured in a shaking incubator under conditions of 30° C. and 180 rpm. During the culturing, absorbance was measured as an optical density (OD) value at a wavelength of 680 nm by using a UV/Visible spectrophotometer to measure degrees of cell growth at each stage.

Figure 2:
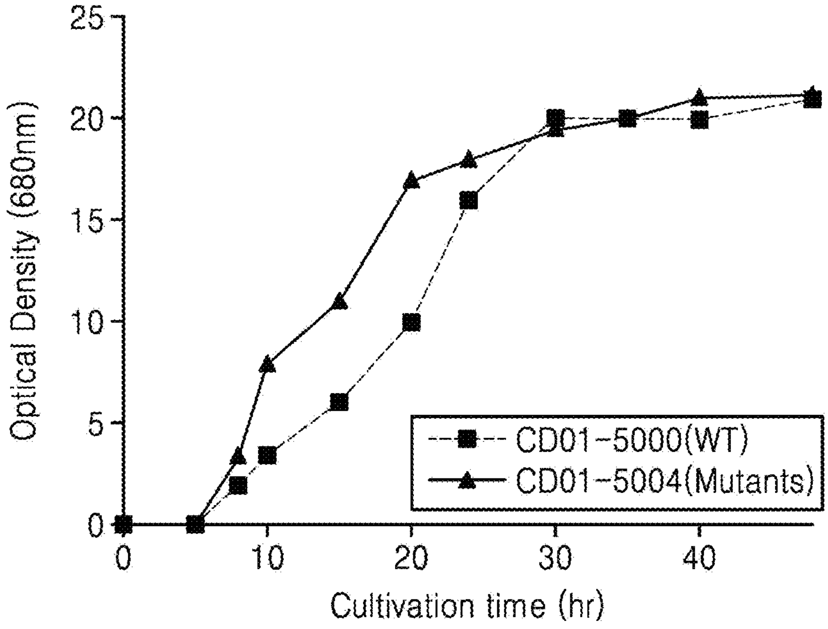
FIG. 2 is a graph of growth curves of *Schizochytrium* sp. strains CD01-5000 and CD01-5004.

As a result, as shown in FIG. 2, the variant CD01-5004 was confirmed to exhibit a sugar consumption rate and cell growth equal to or higher than that of the wild-type strain CD01-5000, and reached the exponential phase about 5 hours faster than the wild-type strain.

Example 6. Confirmation of Growth Characteristics of Wild-Type *Schizochytrium* Sp. Strain CD01-5000, and Mutant *Schizochytrium* Sp. Strain CD01-5004

It was confirmed whether growth was possible in a wide pH range when culturing the novel wild-type *Schizochytrium* sp. strain CD01-5000, and a mutant thereof, *Schizochytrium* sp. strain CD01-5004.

Specifically, the CD01-5000 and CD01-5004 strains were inoculated into GYEP medium having a pH of 2, 3, 3.5, 4, 6, 8, 8.5, 9, or 9.5 each in a 500 mL flask, and cultured in the same manner as described in Example 4, and then the absorbance of each at 0, 24, 40, and 48 hours after initiating the culturing was measured to evaluate degrees of cell growth.

TABLE 6

| Culture time (h) | 0 | 24 | 40 | 48 |
|---|---|---|---|---|
| pH 2 | 1.29 | 0.81 | 0.77 | 0.74 |
| pH 3 | 0.31 | 0.39 | 3.43 | 3.94 |
| pH 3.5 | 0.31 | 18.60 | 20.05 | 20.00 |
| pH 4 | 1.29 | 16.08 | 17.70 | 19.30 |
| pH 6 | 1.29 | 13.52 | 19.30 | 15.75 |
| pH 8 | 1.29 | 13.78 | 18.15 | 16.05 |
| pH 8.5 | 0.31 | 14.05 | 14.55 | 14.20 |
| pH 9 | 0.31 | 4.95 | 15.35 | 12.95 |
| pH 9.5 | 0.31 | 2.35 | 0.30 | 0.64 |

In Table 6, each value is absorbance for each culture time according to pH conditions.

Figure 3:
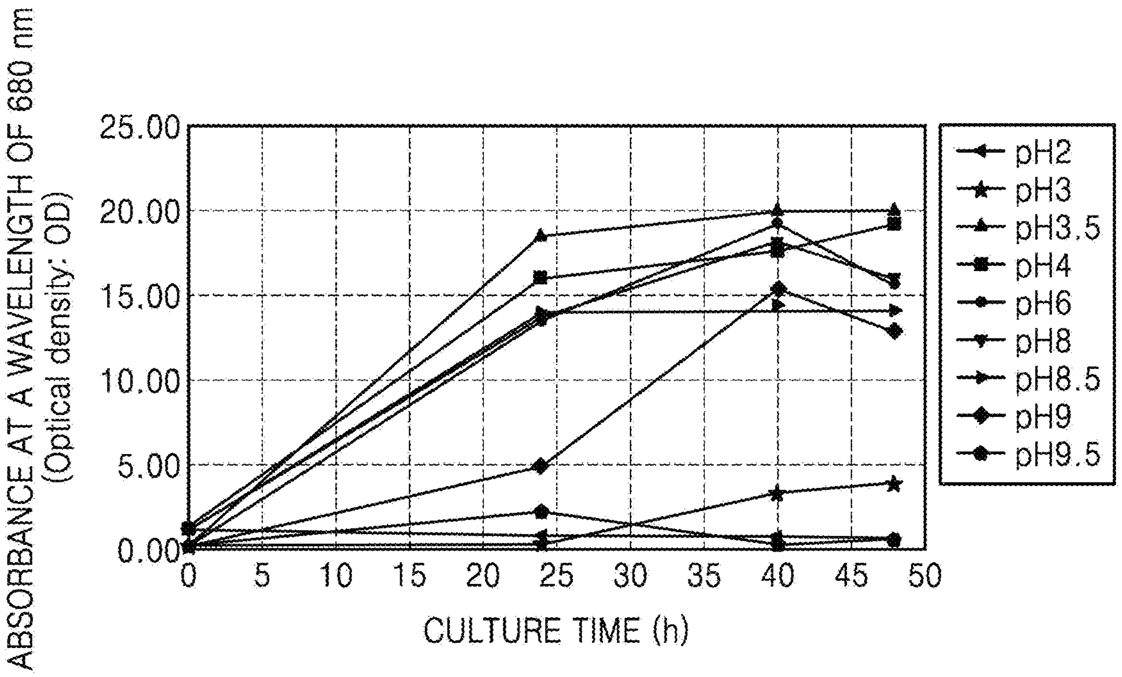
FIG. 3 is a graph of a growth curve of a *Schizochytrium* sp. strain CD01-5004.

As a result, as shown in Table 6 and FIG. 3, it was confirmed that the CD01-5004 strain is capable of growing in a wide range of pH of pH 3.5 to pH 9, and the CD01-5000 strain also showed growth characteristics similar to the above characteristics.

In addition, in view of the fact that the culture medium showed a deep red color when culturing the CD01-5000 and CD01-5004 strains, the strains were found to produce antioxidant pigments of the carotenoid family, such as β-carotene, lutein, astaxanthin, capsanthin, annatto, canthaxanthin, lycopene, β-apo-8-carotenal, zeaxanthin, β-apo-8-carotenal-ester, etc.

From the above description, those skilled in the art to which the present disclosure belongs will be able to understand that the present disclosure may be embodied in other specific forms without changing its technical idea or essential characteristics. Therefore, it should be understood that the above examples are not limitative, but illustrative in all aspects. A scope of the present application should be construed as including all changes or modifications derived from the meaning and scope of the claims to be described later and equivalent concepts, rather than the detailed description above.

The invention claimed is:

1. Microalgae of the genus *Schizochytrium* (*Schizochytrium* sp.), deposited under an accession number of KCTC14345BP, and having an ability to produce docosahexaenoic acid (DHA), eicosapentaenoic acid (EPA), and palmitic acid (PA).

2. The microalgae of claim 1, wherein the microalgae produce 35 wt % to 60 wt % of docosahexaenoic acid based on a total weight of fatty acids.

3. The microalgae of claim 1, wherein the microalgae produce 0.5 wt % to 10 wt % of eicosapentaenoic acid based on a total weight of fatty acids.

4. The microalgae of claim 1, wherein the microalgae produce 10 wt % to 30 wt % of palmitic acid based on a total weight of fatty acids.

5. The microalgae of claim 1, wherein the microalgae have an ability to produce carotenoids.

6. The microalgae of claim 5, wherein the carotenoids are at least one selected from the group consisting of β-carotene, lutein, astaxanthin, capsanthin, annatto, canthaxanthin, lycopene, β-apo-8-carotenal, zeaxanthin, and β-apo-8-carotenal-ester.

7. Biomass comprising: the microalgae of the genus *Schizochytrium* of claim 1, cultures of the microalgae, or dried products of the cultures comprising the microalgae.

8. A feed composition, comprising the biomass of claim 7, or concentrates or dried products of the biomass.

9. A method of preparing biomass derived from microalgae of the genus *Schizochytrium*, comprising:

culturing microalgae of the genus *Schizochytrium*, which are deposited under an accession number of KCTC14345BP, and have an ability to produce docosahexaenoic acid, eicosapentaenoic acid, and palmitic acid; and recovering biomass from the microalgae, cultures of the microalgae, dried products of the cultures, or lysates of the dried products.

10. The method of claim 9, wherein the culturing is performed under heterotrophic conditions.

11. The method of claim 9, wherein the culturing is performed by using a medium comprising a carbon source and a nitrogen source.

12. The method of claim 11, wherein the carbon source is at least one selected from the group consisting of glucose, fructose, maltose, galactose, mannose, sucrose, arabinose, xylose, and glycerol.

13. The method of claim 11, wherein the nitrogen source is:

i) at least one organic nitrogen source selected from the group consisting of yeast extract, beef extract, peptone, and tryptone, or ii) at least one inorganic nitrogen source selected from the group consisting of ammonium acetate, ammonium nitrate, ammonium chloride, ammonium sulfate, sodium nitrate, urea, and monosodium glutamate (MSG).

14. A method of preparing bio-oil derived from microalgae of the genus *Schizochytrium*, comprising:

culturing microalgae of the genus *Schizochytrium*, which are deposited under an accession number of KCTC14345BP, and have an ability to produce docosahexaenoic acid, eicosapentaenoic acid, and palmitic acid; and recovering lipids from the microalgae, cultures of the microalgae, dried products of the cultures, or lysates of the dried products.

* * * * *